(12) United States Patent
Kenneally et al.

(10) Patent No.: US 7,342,136 B2
(45) Date of Patent: Mar. 11, 2008

(54) PROCESS OF MAKING LONG CHAIN INTERNAL FATTY TERTIARY AMINES

(75) Inventors: Corey James Kenneally, Mason, OH (US); Jeffrey John Scheibel, Lebanon, OH (US)

(73) Assignee: Procter & Gamble Company, Cincinnati, OH (US)

( * ) Notice: Subject to any disclaimer, the term of this patent is extended or adjusted under 35 U.S.C. 154(b) by 63 days.

(21) Appl. No.: 11/272,275

(22) Filed: Nov. 10, 2005

(65) Prior Publication Data

US 2006/0106255 A1    May 18, 2006

Related U.S. Application Data

(60) Provisional application No. 60/627,980, filed on Nov. 15, 2004.

(51) Int. Cl.
    *C07C 209/08* (2006.01)
    *C07C 209/12* (2006.01)
    *C07C 291/04* (2006.01)

(52) U.S. Cl. .................. 564/481; 564/296; 564/298

(58) Field of Classification Search ............... None
    See application file for complete search history.

(56) References Cited

U.S. PATENT DOCUMENTS

| | | | |
|---|---|---|---|
| 3,379,764 A * | 4/1968 | Wyness et al. | ............ 564/481 |
| 3,444,205 A | 5/1969 | Frohlich et al. | |
| 3,471,562 A | 10/1969 | Wakeman et al. | |
| 3,497,555 A | 2/1970 | Dudzinski | |
| 3,542,876 A | 11/1970 | Blaney | |
| 3,647,906 A | 3/1972 | Farley | |
| 3,780,107 A | 12/1973 | Chisholm et al. | |
| 4,024,189 A | 5/1977 | Davis | |
| 4,138,437 A | 2/1979 | Strauss et al. | |
| 4,210,605 A | 7/1980 | Hoshino et al. | |
| 4,248,801 A | 2/1981 | Tomidokoro et al. | |
| 4,251,465 A | 2/1981 | Swift et al. | |
| 4,254,060 A | 3/1981 | Kimura et al. | |
| 4,727,203 A | 2/1988 | Hamilton, Jr. | |
| 4,895,997 A | 1/1990 | Hamilton, Jr. et al. | |
| 5,849,974 A | 12/1998 | Clarembeau et al. | |
| 6,281,404 B1 | 8/2001 | Miller | |
| 6,294,514 B1 | 9/2001 | Welling | |

OTHER PUBLICATIONS

U.S. Appl. No. 11/272,559, filed Nov. 10, 2005, Shi et al.
U.S. Appl. No. 11/274,909, filed Nov. 15, 2005, Shi et al.

* cited by examiner

*Primary Examiner*—Brian Davis
(74) *Attorney, Agent, or Firm*—Stephen T. Murphy; Kim W. Zerby; Steve W. Miller

(57) ABSTRACT

A process for preparing long chain internal fatty tertiary amines, quaternary amines and amine oxides via the selection of long chain internal olefins.

38 Claims, No Drawings

PROCESS OF MAKING LONG CHAIN INTERNAL FATTY TERTIARY AMINES

CROSS REFERENCE TO RELATED APPLICATION

This application claims priority under 35 U.S.C. §119(e) to U.S. provisional application No. 60/627,980, filed Nov. 15, 2004.

FIELD OF THE INVENTION

The present invention relates to a hydrohalgenation process for making long chain internal fatty tertiary amine and the corresponding quaternary amines and amine oxides.

BACKGROUND OF THE INVENTION

Linear tertiary amines with chain lengths between 8 and 24 carbon atoms are commonly referred to as fatty tertiary amines. According to Ullman's Encyclopedia of Chemical Technology, 5$^{th}$ edition, Volume A2, these materials, and their derivatives such as the corresponding quaternary ammonium compounds, are widely used in applications such as fabric softeners, drilling muds, surfactants, asphalt emulsifiers, and bactericides/disinfectants.

For fabric softeners, the most effective are the fatty quaternary ammonium compounds dialkyldimethyl ammonium chloride or the corresponding methyl sulfate. For drilling muds, methyl or benzyl quaternary ammonium chlorides produced from dialkyl methylamine are useful. For surfactants, $C_{12}$ or $C_{14}$ based alkyldimethylamine oxide is commonly used. For bactericides and disinfectants, alkyl (benzyl)dimethyl and alkyltrimethyl compounds in which the fatty alkyl group contains 12-14 carbon atoms are most effective against a broad range of organisms. Alternatively, the dialkyldimethyl compounds are most effective when the fatty alkyl group contains 8-10 carbon atoms.

Fatty amines are commonly produced from natural fats and oils or from conventional petrochemical raw materials. Three primary feedstocks are used to make fatty tertiary amines: fatty nitriles, fatty alcohols or aldehydes, and long chain olefins.

Fatty nitriles, which are formed from fatty acids and ammonia over dehydrating catalysts in liquid phase reactors or liquid and vapor-phase reactors at 280-360° C., are reacted either with dimethylamine or with formaldehyde and formic acid to produce N,N-dimethylalkylamines. See U.S. Pat. No. 4,248,801 to Lion Fat & Oil Co. and U.S. Pat. No. 3,444,205 to Hoechst.

Fatty alcohols and aldehydes can be converted into the same product via direct amination in the presence of dimethylamine or other primary or secondary amines at 160° C.-230° C. and low pressure (0.1-0.5 MPa) using copper chromite catalysts (for alcohol feedstocks) or noble metal, copper chelate, or copper carboxylate catalysts (for aldehydes). See U.S. Pat. No. 4,251,465 to Gulf Research and Development Co., U.S. Pat. No. 4,138,437 to Hoechst, and both U.S. Pat. No. 4,254,060 and 4,210,605 to Kao.

Long chain olefins are converted into the corresponding long chain amine products in the presence of dimethylamine or other primary or secondary amines via hydrobromination (with no added catalyst). See U.S. Pat. No. 3,471,562 and U.S. Pat. No. 3,497,555 to Millmaster Onyx, and U.S. Pat. No. 4,024,189 to Ethyl Corp.

These processes, however, produce a high content of terminal amines, typically 91 wt % or greater by weight of the amine. As used herein "terminal amines" means that the amine moiety is connected on the α or β carbon of the long chain alkyl chain of the amine.

For the case of amine oxide surfactants, this is done to provide good cleaning with high suds stability. However, sometimes it is desirable to produce with a high content (10 wt % or greater by weight of the amine) of internal amine. This would be useful for branched chain surfactants with improved cold water cleaning, moderate suds stability, and improved wetting properties.

Therefore, there is a need for a commercially feasible process for making long chain fatty tertiary amines and amine oxides which provide the desired content of internal amines, using hydrocarbons from a variety of sources. A secondary objective is to produce these amines via a low cost, economical process.

SUMMARY OF THE INVENTION

The present invention relates to a process comprising the steps of (a) obtaining a long chain internal olefin source selected from the group consisting of oligomerized $C_2$-$C_{11}$ olefins, metathesized $C_5$-$C_{10}$ olefins, Fischer-Tropsch olefins, dehydrogenated long chain paraffin hydrocarbons, thermally cracked hydrocarbon waxes, or dimerized vinyl olefins and mixtures thereof; (b) reacting via hydrohalogenation the internal olefin source with a primary amine or a secondary amine to produce long chain internal fatty tertiary amines; (c) optionally separating any unconverted hydrocarbons and color or odor bodies from the long chain fatty tertiary amines resulting in a purified long chain fatty tertiary amine product; (d) optionally oxidizing the long chain fatty tertiary amine to the corresponding amine oxide; and (e) optionally quaternizing the long chain fatty tertiary amine into a quaternary long chain internal fatty tertiary amine product.

DETAILED DESCRIPTION OF THE INVENTION

As used herein "long chain internal olefin" means an olefin with 8 to 22 carbon atoms and greater than 10%, 50%, 70%, 90% and up to 100% of olefins comprise the carbon-carbon double bonds being in a position other than the terminal (α and/or β carbon) position on the olefin. The long chain internal olefin may be linear or branched. If the long chain internal olefin is branched, a $C_1$-$C_5$ carbon branch is preferred.

As used herein "internal amine" means an amine having the amine moiety attached to the alkyl moiety in greater than 10%, 50%, 70%, 90% and up to 100% of the amines in a position other than the terminal (α+β carbon) position on the alkyl moiety.

Incorporated and included herein, as if expressly written herein, are all ranges of numbers when written in a "from X to Y" or "from about X to about Y" format. It should be understood that every limit given throughout this specification will include every lower or higher limit, as the case may be, as if such lower or higher limit was expressly written herein. Every range given throughout this specification will include every narrower range that falls within such broader range, as if such narrower ranges were all expressly written herein.

Without being limited by theory, it is believed that low cost production of long chain internal fatty tertiary amines is best accomplished by a process which uses low cost feedstocks, as manufacturing costs for a high volume, efficient chemical process are generally dominated by raw materials costs. Of the feedstocks available to produce long chain fatty tertiary amines, olefins are generally among the lowest cost materials. While alpha olefins are used to make terminal tertiary amines, long chain internal amines require a source of long chain internal olefins.

Long chain internal olefin sources can be obtained from a variety of different processes, including $C_2$-$C_{11}$ olefin oligomerization processes, $C_5$-$C_{10}$ olefin metathesis processes, Fischer-Tropsch processes, catalytic dehydrogenation of long chain paraffin hydrocarbons, thermal cracking of hydrocarbon waxes and dimerized vinyl olefin processes.

The long chain internal olefins from any of the above described processes are then reacted with primary alkyl amines or secondary alkyl amines to produce long chain fatty tertiary amines using commercially feasible processes such as hydrohalogenation. Any unconverted hydrocarbons and color or odor bodies are subsequently separated from the long chain internal fatty tertiary amines using distillation or other commercial techniques.

In the optional final step of the present process, the long chain internal fatty tertiary amines are converted into the corresponding amine oxide via oxidation.

The processes and methods herein may include a wide variety of other variations. The processes and methods of the present invention are described in detail hereinafter.

The present process relates to converting long chain internal olefins to long chain internal fatty tertiary amines and optionally, long chain internal amine oxides.

Long Chain Internal Olefin Sources

Oligomerized $C_2$-$C_{11}$ Olefins

Long chain internal olefin sources from oligomerized $C_2$-$C_{11}$ olefins are readily available from a variety of sources, including natural gas, naptha, and gas oil fractions. Oligomerized ethylene is available from suppliers such as Shell Chemicals, Exxon Chemicals, BP Amoco and Chevron Phillips.

The oligomerized $C_2$-$C_{11}$ olefins may be derived from $C_2$-$C_{11}$ olefins in the presence of either organoaluminum compounds, transition metal catalysts or acidic zeolites to produce a wide range of chainlengths that is further purified by various known means, preferably distillation. See U.S. Pat. Nos. 3,647,906, 4,727,203, and 4,895,997 to Shell Oil Co., U.S. Pat. No. 5,849,974 to Amoco Corp., and U.S. Pat. No. 6,281,404 to Chevron Chemicals which disclose suitable catalysts and processing conditions for ethylene oligomerization.

Oligomerization includes the production of dimers, trimers, or tetramers using catalysts such as acidic zeolites, nickel oxides, or metallocene catayists. For example, U.S. Pat. No. 5,026,933 discusses the use of highly siliceous ZSM-23 zeolite catalyst for propylene oligomerization. Other suitable catalysts include AMBERLYSTTM™ 36 (bead form, macroreticular, sulfonic acid ion exchange resin catalyst from Rohm and Haas) and acidic zeolites including mordenite, offretite and H-ZSM-12 in at least partially acidic form. See also *Comprehensive Organic Transformation*, $2^{nd}$ Edition, Larock, Richard C., pages 633-636; and *Vogel's Textbook of Practical Organic Chemistry*, $5^{th}$ Edition, Furniss, Brian S., Hannaford, Antony J., Smith, Peter W.G., and Tatchell, Austin R., pages 574-579.

Depending on the supplier and the process used, either α-olefins or internal olefins are generated from the oligomerization processes. For the case of α-olefin feedstocks or mixed α-olefin and internal olefin feedstock, an isomerization step is required to generate the desired long chain internal olefins. The isomerization step results in random placement of the double bond along the carbon chain. Suitable isomerization catalysts include homogeneous or heterogeneous acidic catalysts, supported metal oxides such as cobalt oxide, iron oxide, or manganese oxide, and metal carbonyls such as cobalt carbonyl and iron carbonyl. See U.S. Pat. Nos. 3,647,906, 4,727,203, and U.S. Pat. No. 4,895,997 to Shell Oil Co., U.S. Pat. No. 5,849,974 to Amoco Corp., and U.S. Pat. No. 6,281,404 to Chevron Chemicals which disclose suitable catalysts and processing conditions for double bond isomerization.

Metathesis of $C_5$-$C_{10}$ Olefins

Cross-metathesis of $C_5$-$C_{10}$ olefins with other olefins or even with oleochemicals can be used to produce suitable long chain internal olefins for the present process. For example, two octene molecules can be reacted to form tetradecene and ethylene. Or the methyl ester of oleic acid can be reacted with hexene to form dodecene and the methyl ester of lauric acid. Common homogeneous catalysts include the ruthenium based Grubb's catalyst as well as the Schrock catalyst. Cross metathesis is further described in the text *Olefin Metathesis and Metathesis Polymerization* by Ivin and Mol (1997), and also the journal Chemical and Engineering News, vol. 80, no. 51, Dec. 23, 2002, pp. 29-33.

Other Internal Olefins

Alternative processes for olefins are from the isomerization/disproportionation olefin process and/or the Shell higher olefin process (SHOP) process from Shell Chemical. These are commercially available materials under the tradename NEODENE™.

Fischer-Tropsch Olefins and Paraffins

Long chain internal olefin sources from Fischer-Tropsch involves converting a source of carbon such as coal, methane, or natural gas to a wide distribution of carbon chainlengths and then isolating a narrow hydrocarbon fraction, using techniques such as distillation or liquid-liquid extraction.

Two different catalysts are commercially used: iron and cobalt, with iron generally producing a higher yield of olefins and cobalt producing a higher yield of paraffins. Hydrocarbons recovered from the Fischer-Tropsch reaction may be a mixture of linear and branched chains, olefins and paraffins, having both terminal and internal double bonds. Straight run Fischer-Tropsch olefin and paraffins from jet and/or diesel fractions may be utilized in the present process.

As disclosed above, double bond isomerization catalysts can be employed to convert α-olefins to internal olefins. Paraffins present in the internal olefin feed stream may be left with the internal olefins until amination is complete.

For the iron based Fischer-Tropsch reaction product, it may be desirable for oxygenates to be separated out from the hydrocarbons prior to amination. Oxygenates refer to carboxylic acids, alcohols, aldehydes, and ketones, which chainlengths from $C_1$ to $C_{18}$. Oxygenates impart undesirable color, odor, and performance impurities to tertiary amines and must be removed from the hydrocarbons prior to amination or from the crude tertiary amine after amination.

There are several methods to separate oxygenates from Fischer-Tropsch crude prior to amination. Liquid-liquid extraction is the preferred process for separating oxygenates from hydrocarbons. Liquid-liquid extraction is effective in removing both alcohols and carboxylic acids from hydrocarbons and can be achieved with more reasonable capital investment than distillation or adsorption. Caustic treatment, followed by centrifuging, water washing, or filtration is effective in neutralizing and separating carboxylic acids, but has no effect on alcohols.

Use of liquid-liquid extraction to remove oxygenates can be done with a wide variety of solvents. For example, diethylene glycol is reported to be a solvent for removal of aromatics from reformate, and propane is reported to be a solvent for removal of fatty acids from natural oils. See *Packed Tower Design and Applications*, 2$^{nd}$ Ed., Strigle, page 294. A wide variety of factors must be considered in the choice of the proper solvent, including solubilities, interfacial tension, differences between phase densities, viscosity, corrosion, and cost. Solvent polarity index is an important indicator of the solubility of the oxygenates as well as insolubility of the hydrocarbons. For a description of polarity index see *Practical HPLC Development*, 2$^{nd}$ Ed., Snyder, Kirkland, and Glajch, page 723; and *Introduction to Modern Liquid Chromatography*, 2$^{nd}$ Ed., Snyder and Kirkland, pages 258-260. Applicants have found that it is preferred to use solvents with Fischer-Tropsch with a polarity index of 5.6 to 6.0. One suitable solvent is an 80/20 wt % mixture of ethanol/water. Temperature of operation for liquid extraction is from 20° C. to just below the boiling point of the solvent selected. Solvent to feed ratios of 0.1 to 3 are preferred.

Extraction can be carried out in three classes of equipment: mixer-settlers, contacting columns, or centrifugal contactors. When only one stage of separation is required for the extraction step, a mixer-settler may used. Spray columns may be used when the density difference between the phases is large. When more than three stages of separation are needed, packed or tray columns with countercurrent flow are the preferred devices. Centrifugal contactors may also used if the liquid phases have small density difference and a large number of equilibrium stages are needed. When ten to twelve equilibrium stages are required, a mechanical contactor with rotating disks or impellers is often used, as these have higher efficiencies than the packed contactors. The preferred number of equilibrium stages is one to twelve.

In theory, distillation can be used to separate oxygenates from hydrocarbons, but the boiling points of oxygenates and hydrocarbons can overlap so that distillation is not preferred. Bulk separation by adsorption using molecular sieves is also possible, but expensive from a capital investment standpoint.

Dehydrogenation of Long Chain Hydrocarbons

Long chain internal olefin sources may also be obtained from the catalytic dehydrogenation of long chain paraffins or paraffin/olefin mixtures which yields long chain olefins with the same number of carbon atoms and with random locations of a double bond along the chain. As disclosed above, double bond isomerization catalysts can be employed to convert α-olefins to internal olefins. Paraffins present in the internal olefin feed stream may be left with the internal olefins until amination is complete.

Sources include the kerosene fraction from petroleum refineries and Fischer-Tropsch paraffins or paraffiii/olefin mixtures. See U.S. Pat. No. 3,531,543 to Chevron Research and U.S. Pat. Nos. 3,745,112, 3,909,451, and 4,608,360 to UOP which discuss suitable catalysts and processing conditions for paraffin dehydrogenation. Straight run Fischer-Tropsch olefin and paraffins from jet and/or diesel fractions may be utilized in the catalytic dehydrogenation process. The UOP PACOL™ process, a process of dehydrogenation of heavy n-paraffins via heterogeneous platinum catalysts supported on an alumina base, operates at 450° C. to 510° C. and 0.3 MPa using a platinum on alumina catalyst, promoted by lithium, arsenic, or germanium. To minimize by-products, low conversion rates of 10-15 wt % are used. Use of the low conversion rate results in paraffin-olefin mixtures that may be further separated and purified by the UOP OLEX™ process for separating olefins from paraffins, or reacted together with amine before paraffin separation is done.

Thermally Cracked Hydrocarbon Waxes

Long chain internal olefins may also be derived from thermal cracking of hydrocarbon waxes from either petroleum streams or the Fischer Tropsch reactions, including Fischer Tropsch paraffin waxes. The chainlength of these waxes is generally greater than $C_{22}$. Thermal cracking is a non catalytic, free radical process conducted at high temperatures in the presence of steam, followed by distillation to separate and recycle the unreacted wax to the cracking furnace.

A tubular furnace is preferably used for the cracking reaction. The temperature for the thermal cracking ranges from 400-600° C. Selection of higher temperatures are not desired as higher temperatures results in the formation of shorter chain olefins (a chainlength less than $C_5$), higher levels of polyolefins, as well as more gas products. Selection of lower temperatures are not desired as lower temperatures reduce the conversion of long chain internal olefins per pass, which is undesirable from a capital cost standpoint.

The pressure in the thermal cracking reaction zone is 0.1-1 MPa. Higher pressure generally leads to an increase in the yield of liquid products, with a corresponding reduction in (α-olefin content. Space velocity is 1.25-5.0 volume of feed/volume of reactor/hour. This corresponds approximately to a vapor residence time in the reactor of 2.5-10 seconds. Higher residence time is undesirable as it leads to increased decomposition and secondary by-products verses the desired long chain internal olefins. The conversion per pass in the reaction is 10-25 wt %.

Gas and liquid products from the thermal cracking reactor are separated by a distillation step using a pressure of 10-2500 Pa and a temperature of 100° C.-280° C. Any unreacted wax is taken as a bottom fraction from the distillation step and recycled back to the thermal cracking furnace and mixed with fresh hydrocarbon waxes. As disclosed above, double bond isomerization catalysts may be employed to convert any α-olefins present to long chain internal olefins.

Internal Vinylidenes

Internal vinylidenes may also be utilized as the long chain internal olefin source of the present process. Vinylidenes may be produced via a process involving dimerizing vinyl olefin with at least one trialkylaluminum compound. Further conditions may be found in U.S. Pat. No. 5,625,105. Vinylidenes may also be produced via a process of dimerizing a vinyl-olefin monomer in the presence of a tri-alkyl aluminum catalyst as described in U.S. Pat. No. 4,973,788.

Reaction of Long Chain Internal Olefins with Primary or Secondary Amines Using Hydrohalogenation Conditions The long chain fatty tertiary amines desired in the present process are produced by the reaction between the long chain internal olefins as described above and either a primary or secondary alkyl amine. If a primary alkyl amine such as monomethylamine is used, then two long chain internal olefin molecules are added to the primary alkyl amine to produce a di-long chain fatty tertiary monoalkyl amine product. If a secondary alkyl amine such as dimethylamine is used, then one long chain internal olefin molecule is added to the secondary alkyl amine to produce a mono-long chain fatty tertiary dialkyl amine product.

Initiators may optionally be utilized for the hydrohalogenation step such as ozone, lauroyl peroxide and or t-butyl peroxide. Reaction conditions when initiators are utilized include temperatures from 55-65° C. and pressures from 0.2-5.5 MPa for primary alkyl amine usage to produce di-long chain fatty mono alkyl amine product. Reaction conditions when initiators are utilized include temperatures from 70-145° C. and pressures from 0.2-5.5 MPa for secondary alkyl amine usage to produce mono-long chain fatty dialkyl amine product.

Halogens such as bromine, chlorine, and iodine may be utilized for the hydrohalgenation step of the present process.

Tertiary amine products that are produced by the process of the present invention have an internal amine content of from 10 wt % to 100 wt %, a linear olefin content of from about 1 wt % to 100 wt %, and a paraffin content of from 0 wt % to about 90 wt %.

Examples of desirable tertiary amine products of the present process include, but are not limited to: trioctylamine, tridecylamine, tridodecylamine, didodecylmethylamine, ditetradecylmethylamine, dihexadecylmethylamine, dioctadecylmethylamine, decyldimethylamine, dodecyldimethylamine, tetradecyldimethylamine, hexadecyldimethylamine, and octadecyldimethylamine. The amine moiety of these materials is located on the long chain alkyl in an internal position. An internal position refers to a carbon other than the α or β carbon of the long chain alkyl.

Hydrohalogenating and aminating a single long chain internal olefin described above produces by the present process a long chain internal fatty tertiary amine with the following formula (I):

formula (I)

wherein $R_1$ and $R_2$ of formula (I) independently are linear or semi-linear hydrocarbons with a chainlength of 1 to 20 carbon atoms. As used herein "semi-linear" means that $R_1$ and/or $R_2$ of formula (I) comprise between 1 and 4 $C_1$-$C_3$ alkyl branches randomly distributed or evenly distributed. The long chain internal fatty amine structure is such that an alkyl portion has a total sum of carbons from 8 to 22 carbon atoms. As used herein, the alkyl portion is $R_1$+$R_2$+carbon between the nitrogen (hereinafter referred to as C carbon) of formula (I).

In a preferred embodiment, the total sum of carbons in the alkyl portion ($R_1$+$R_2$+C carbon) of formula (I) is from 10 to 20 carbon atoms, preferably from 12 to 18, more preferably from 10 to 14. The number of carbon atoms for $R_1$ of formula (I) may be approximately the same number of carbon atoms for $R_2$ of formula (I) such that $R_1$ and $R_2$ of formula (I) are symmetric. As used herein "symmetric" means that for carbon atoms, $|R_1-R_2|$ is less than or equal to 5 carbon atoms in at least 50 wt %, more preferably at least 75 wt % to 100 wt % of the long chain fatty internal amine produced herein. In another embodiment $|R_1-R_2|$ is less than 4, or less than 3 carbon atoms.

The process of the present application comprises a hydrohalogenation step; such as hydrobromination, hydrochlorination, or hydroiodination; having an initiator selected from ozone, lauroyl peroxide, or t-butyl peroxide at a concentration of 10-2000 ppm to produce a primary or secondary alkylbromide product. Process conditions for the hydrohalogenation step are a temperature of 5-60° C. pressure of 0.1-1 MPa, and reaction time of 0.1-5.0 hours. Higher pressure (0.5-1.0 MPa) is preferred to keep the hydohalide acid, such as hydrobromic acid, hydrochloric acid, or hydroiodic acid in solution. Higher temperatures (25-60° C.) are generally used for longer chainlengths.

After the hydrohalogenation step, the primary or secondary alkylhalide product is reacted with a primary or secondary amine to form a tertiary amine-halide complex. Process conditions for the production of the tertiary amine-halide complex are a temperature of 55-65° C. for amination of primary (terminal) alkylhalide (alkylbromide, alkylchloride, alkyliodide and any mixtures thereof) and a temperature of 70-145° C. for amination of secondary (nonterminal) alkylhalide (alkylbromide, alkylchloride, alkyliodide and any mixtures thereof). A pressure of 0.2-5.5 MPa is selected as such to keep the primary or secondary amine in solution. A molar ratio of primary or secondary amine to primary or secondary alkylhalide product ranging from 1:1 to 25:1 moles is used to maximize conversion in the amination process. The reaction time is 0.1 to 5.0 hours. After reaction is completed, water and sodium hydroxide are mixed in with the desired tertiary amine product and then a phase separation step is utilized to create a two phase system.

After settling of the two phases, the process further comprises the step of recovering an organic layer that consists of tertiary amine product and unreacted long chain internal olefin, along with a water layer comprising sodium halide, water, and unreacted primary or secondary alkyl amine.

Optional Purification of the Internal Fatty Tertiary Amines Using Thermal Separation Techniques The process of the present invention further comprises the step of purifying the long chain internal fatty tertiary amine product from the previous step to form a purified long chain internal fatty tertiary amine product. Preferred purity of the purified long chain internal fatty tertiary amine product is from about 95 wt % or greater, more preferably from about 97 wt % or greater, most preferably from about 98 wt % to about 100 wt % by weight of the purified long chain internal fatty tertiary amine product after the purification step.

The crude long chain internal fatty tertiary amine products may be mixed with paraffins, unreacted olefins, alkylhalides, color and odor bodies, and small quantities of oxygenates such as alcohols or carboxylic acids among other impurities.

Many of the impurities listed above may be removed via thermal separation techniques. A preferred purification step is via flash stills and/or topping columns to give a purified internal fatty tertiary amine. Equipment for the flash still and the topping column includes falling film evaporators, thin film evaporators, wiped film evaporators, reboiler flash units, and multistage distillation columns. All equipment is known to one of skill in the art and available from suppliers such as Pfaudler, Lewa, and Swenson. Heavy impurities such as polyalkylamines, salts, and color bodies may be removed in a bottom stream of a flash still operating under a pressure of 10 Pa-2500 Pa (0.1-20 mm Hg) and a temperature of 90-250° C. Light impurities such as residual hydrocarbons (olefin or paraffin) and color bodies may be removed in overhead stream of a topping column operating under a pressure of 10 Pa-2500 Pa (0.1-20 mm Hg) and a temperature of 90-205° C.

Optional Oxidation Step of the Purified Internal Fatty Tertiary Amines

The process of the present invention further comprises the optional step of oxidizing the purified long chain internal fatty tertiary amine to give an oxidation product of the corresponding long chain internal fatty amine oxide. Oxidation of the long chain internal fatty tertiary amine produces by the present process a long chain internal fatty tertiary amine oxide with the following formula (II):

formula (II)

wherein $R_1$ and $R_2$ of formula (II) independently are linear or semi-linear hydrocarbons with a chainlength of 1 to 20 carbon atoms. As used herein "semi-linear" means that $R_1$ and/or $R_2$ of formula (II) comprise between 1 and 4 $C_1$-$C_3$ alkyl branches randomly distributed or evenly distributed. The long chain internal fatty amine oxide structure is such that an alkyl portion has a total sum of carbons from 8 to 22 carbon atoms. As used herein, the alkyl portion is $R_1+R_2+$ carbon between the nitrogen (hereinafter referred to as C carbon) of formula (II).

In a preferred embodiment, the total sum of carbons in the alkyl portion ($R_1+R_2+C$ carbon) of formula (II) is from 10 to 20 carbon atoms, preferably from 12 to 18, more preferably from 10 to 14. The number of carbon atoms for $R_1$ of formula (II) may be approximately the same number of carbon atoms for $R_2$ of formula (II) such that $R_1$ and $R_2$ of formula (I) are symmetric. As used herein "symmetric" means that for carbon atoms, $|R_1-R_2|$ is less than or equal to 5 carbon atoms in at least 50 wt %, more preferably at least 75 wt % to 100 wt % of the long chain fatty internal amine produced herein. In another embodiment $|R_1-R_2|$ is less than 4, or less than 3 carbon atoms.

The purified long chain internal fatty tertiary amine may optionally be converted into using materials such as 5-70 wt % hydrogen peroxide. As described in U.S. Pat. No. 6,294,514 to Procter & Gamble Co., purified long chain internal fatty tertiary amines are typically combined with 5-70 wt % hydrogen peroxide, 0.3-2.5% of a bicarbonate material such as sodium bicarbonate or potassium bicarbonate, and optionally water, to result in an oxidation product which is 30-38 wt % by weight of the oxidation product of the corresponding long chain internal fatty amine. The amount of hydrogen peroxide is 100-115% of stoichiometric to the amount of amine present. The oxidation step target temperature is about 40-100° C. (60-70° C. preferred), and pressure is 0.1 MPa.

The oxidation step is complete when the residual hydrogen peroxide level is below 1%, preferably below 0.1 wt % of the final product composition. Reaction time is generally 4 to 24 hours. Residual hydrogen peroxide is typically decomposed by holding the material at reaction temperature. If necessary, 0.1-5 wt % by weight of the reagents of platinum on alumina may be used as an adsorbent to remove residual hydrogen peroxide from the oxidation product.

Optional Quaternization Step of the Purified Internal Fatty Tertiary Amines

The process of the present invention may further comprise the optional step of quaternizing the purified long chain internal fatty tertiary amine to give a quaternary long chain internal fatty tertiary amine product. Quaternization may be achieved by a reaction of the purified long chain internal fatty tertiary amine with methyl chloride or dimethyl sulfate. Quaternization with methyl chloride is achieved by reaction with 1.0 to 1.3 mole equivalents of methyl chloride relative to the purified long chain internal fatty tertiary amine in an autoclave with temperature range of room temperature (20° C.) to 80° C. under nitrogen pressure from 101 kPa -10100 kPa (1 atm -100 atm). Dimethyl sulfate is reacted at 1.0 to 1.1 mole equivalents relative to the purified long chain internal fatty tertiary amine in a flask blanketed with nitrogen at 10° C. to 70° C. to form the desired quaternary long chain internal fatty tertiary amine product.

EXAMPLES

The following examples further describe and demonstrate embodiments within the scope of the present invention. These examples are given solely for the purpose of illustration and are not to be construed as limitations of the present invention, as many variations thereof are possible without departing from the spirit and scope of the invention.

Example 1

Isomerization of $C_{14}$ α-Olefin, Followed by Hydrobromination, Amination, Purification, and Conversion to Amine Oxide Step 1

Isomerize the $C_{14}$ α-olefin using an acid resin catalyst (AMBERLYST™ 36), pan dried at 110° C. for 48 hours). Add 100 grams of $C_{14}$ α-olefin to a 1 liter flask with agitation and a heating mantle. Add 5 grams of dried AMBERLYST™ 36, heat to 100-120° C., and mix for 24 hours at atmospheric pressure. GC analysis of the product indicates that 90% of the α-olefin was converted to internal olefin with about 3% dimer ($C_{28}$) olefin present.

Alternative Step 1:

Add from a container a mixture of 15.1 g of 1-decene (NEODENE™ 10), 136.6 g of 1-dodecene (NEODENE™ 12) and 109.1 g of 1-tridecene to a 7.57 L (2 gallon) stainless steel, stirred autoclave along with 70 g of a shape selective catalyst (acidic beta zeolile catalyst ZEOCAT™ PB/H). NEODENE™ 10 and 12 are commercially available olefins from the Shell Chemical Company. Wash the residual olefin and catalyst in the container into the autoclave with 200 mL of n-hexane and seal the autoclave. Purge the autoclave twice with 1724.25 kPa (250 psig) nitrogen gas, and then charged to 413.82 kPa (60 psig) nitrogen gas. Stir and heat the mixture to 170° C. to 175° C. for about 18 hours then cool to 70° C.-80° C. Open the valve leading from the autoclave to a benzene condenser and collection tank. Heat the autoclave to about 60° C. then continue to heat to 120° C. with continuous collection of hexane in collection tank. No more hexane should be collected by the time the reactor reaches 120° C. Cool the reactor to 40° C. and pump with mixing 1 kg of n-hexane into the autoclave. Drain the autoclave to remove the reaction mixture product. Filter the reaction mixture product to remove catalyst and evaporate the n-hexane under low vacuum. Distill the reaction mixture product under high vacuum (133 Pa-667 Pa [1-5 mm of Hg]) to give an internal olefin mixture. Collect about 210 g of the internal olefin mixture at a temperature of 85° C.-150° C.

Step 2

Hydrobrominate the $C_{14}$ internal olefin using lauroyl peroxide catalyst. Add 100 grams of isomerized $C_{14}$ olefin from step 1 to a 1 liter flask with agitation and a heating mantle. Add 0.024 grams of lauroyl peroxide, heat to 20-60° C., bubble hydrogen bromide gas into the flask at a flowrate of 0.4 grams/min. Mix for 2 hours, then stop the flow of hydrogen bromide and cool down. GC analysis of the product indicates that 99% of the olefin (both α-olefin and internal olefin) are converted into $C_{14}$ alkyl bromide.

Step 3

Aminate the $C_{14}$ alkyl bromide using dimethylamine. Add 50 grams of $C_{14}$ alkylbromide from step 2 to a 1 liter Parr autoclave. Add 106 grams of dimethylamine to the reactor to achieve a target molar ratio of 12:1 dimethylamine:alkyl bromide. Turn on the agitator and slowly heat the reactor to about 140° C. over a period of 75 minutes. Pressure in the reactor will slowly rise to about 1379.4 kPA (200 psig). Hold the reactor at 140° C. for about 5 minutes, then slowly cool the reactor to 20° C. over about 2 hours. Depressurize the reactor by venting off excess DMA, then empty out. GC analysis of the product indicates that a large majority of the alkylbromide is converted, with at least 95% selectivity to $C_{14}$ alkyldimethylamine (crude amine).

Step 4

Purification of the $C_{14}$ Alkyldimethylamine

Phase separate and distill the $C_{14}$ alkyldimethylamine product. Prepare a premix consisting of 10 grams of 50% sodium hydroxide solution and 50 grams of deionized water. Combine the crude amine from step 3 with the premix in a 1 liter flask with agitation at 20° C. for 15 minutes. Stop the agitation and transfer the mixture to a separatory flask to separate into two phases. The bottom layer will consist of sodium bromide, water, and dimethyl amine while the top layer will consist of tertiary amine, dimethylamine and trace amounts of hydrocarbons, alkylbromides, color and odor bodies. Decant the top layer and place in a flask. Sparge the top layer with nitrogen to remove any volatiles. Short path distill the sparged top layer using a Kugelrohr apparatus at a temperature of 135° C. and a pressure of 65 Pa (0.5 mm Hg). A dark colored bottoms, consisting of olefin dimer and dialkylamine will be left behind in the apparatus, along with a small amount of highly volatile odor and color bodies. Approximately 95% of the top layer is distilled as a colorless product, consisting primarily of $C_{14}$ alkyldimethylamine (distilled amine).

Step 5

Preparation of $C_{14}$ Alkyldimethylamine Oxide

Prepare a premix consisting of 149 grams deionized water and 1.36 grams sodium bicarbonate. Combine the distilled amine from step 4 with the premix in an agitated flask along with 20 grams of 50% hydrogen peroxide. Mix the flask at a temperature of 50-65° C. for 16 hours. The result will be a product with approximately 30 wt % active amine oxide and a residual peroxide level of less than 1 wt % (of the $C_{14}$ alkyldimethylamine oxide product).

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process comprising the steps of:
   a) obtaining a long chain internal olefin;
   b) reacting the internal olefin with a primary amine or a secondary amine to produce long chain internal fatty tertiary amines via hydrobromination and amination, wherein:
      i) the hydrobromination comprises a reaction of the internal olefin and hydrogen bromide gas in a solvent-free environment to form an alkyl bromide, and
      ii) the amination comprises a reaction of the alkyl bromide with a primary amine or secondary amine in a solvent-free environment;
   c) optionally separating any unconverted hydrocarbons and color or odor bodies from the long chain internal fatty tertiary amines resulting in a purified long chain internal fatty tertiary amine product.

2. The process of claim 1 wherein the process further comprises step (c) and further comprises the step of:
   d) oxidizing the purified long chain fatty tertiary amine product into a fatty amine oxide product.

3. The process of claim 1 wherein the process further comprises step (c) and further comprises the step of:
   e) quaternizing the long chain fatty tertiary amine product to form a quaternary long chain internal fatty tertiary amine product.

4. The process of claim 1 wherein the long chain internal olefin is selected from the group consisting of oligomerized $C_2$-$C_{11}$ olefins, methathesized $C_5$-$C_{10}$ olefins, Fischer-Tropsch olefins and paraffins, dehydrogenated long chain paraffin hydrocarbons, thermally cracked hydrocarbon waxes, dimerized vinyl olefins and mixtures thereof.

5. The process of claim 1 wherein the long chain internal olefin is selected from oligomerized $C_2$-$C_{11}$ olefins wherein the oligomerized $C_2$-$C_{11}$ olefins are obtained from an oligomerization step utilizing an organoaluminum compound catalyst, a transition metal catalyst, an acidic zeolite catalyst, a nickel oxide catalyst, or a metallocene catalyst to produce the long chain internal olefin.

6. The process of claim 5 wherein the long chain internal olefin is further subjected to an isomerizing step that converts any α-olefin to internal olefin utilizing an acidic catalyst, a metal oxide catalyst, or a metal carbonyl catalyst.

7. The process of claim 1 wherein the long chain internal olefin is selected from Fischer Tropsch olefins, paraffin and mixtures thereof.

8. The process of claim 7 wherein the long chain internal olefin is further subjected to an isomerizing step that converts any α-olefin to internal olefin utilizing an acidic catalyst, a metal oxide catalyst, or a metal carbonyl catalyst.

9. The process of claim 1 wherein before step (b), the process further comprises the step of removing $C_1$ to $C_{18}$ oxygenates via liquid-liquid extraction, caustic treatment, distillation, molecular sieves, and mixtures thereof.

10. The process of claim 9 wherein the removing step is selected as liquid-liquid extraction via the use of a solvent having a polarity index of 5.6 to 6.0.

11. The process of claim 10 wherein the removing step is carried out at a temperature from about 20° C. to a temperature just below the boiling point of the solvent selected; wherein the ratio of solvent to long chain internal olefin used in the extraction is from 0.1 to 3.

12. The process of claim 9 wherein the oxygenates are selected from carboxylic acids, alcohols, aldehydes, ketones and mixtures thereof.

13. The process of claim 10 wherein the removing step utilizes mixer-settlers, contacting columns, or centrifugal contactors.

14. The process of claim 13 wherein in the removing step comprises from 1 to 12 equilibrium stages.

15. The process of claim 14 wherein the removing step comprises 10 to 12 equilibrium stages and contacting columns are utilized; wherein the contacting columns are packed or tray columns with countercurrent flow.

16. The process of claim 1 wherein the long chain internal olefin is selected from dehydrogenated long chain paraffins or paraffin/olefin mixtures.

17. The process of claim 1 wherein the long chain internal olefin is selected from thermal cracked hydrocarbon waxes from petroleum streams or Fischer-Tropsch reactions wherein the long chain internal olefin is produced from the step of heating the hydrocarbon waxes in a tubular furnace from 400-600° C.; 0.1-1 MPa; a space velocity of from 1.25 to about 5.0 volume of feed/volume of reactor/hour; and a conversion per pass in the reaction is 10-25 wt %.

18. The process of claim 17 wherein the long chain internal olefin is further subjected to an isomerizing step that converts an α-olefin to internal olefin utilizing and isomerization catalyst.

19. The process of claim 1 wherein the long chain internal olefin is selected from internal vinylidene produced by dimerizing vinyl olefin.

20. The process of claim 1 wherein step (b) comprises the use of a primary alkyl amine such that for every one molecule of primary alkyl amine, two molecules of a long chain internal olefin from the long chain internal olefin is added to produce a di-long chain fatty tertiary amine product.

21. The process of claim 1 wherein step (b) comprises the use of a secondary alkyl amine such that for every one molecule of secondary alkyl amine, one molecule of a long chain internal olefin from the long chain internal olefin is added to produce a mono-long chain fatty tertiary amine product.

22. The process of claim 1 wherein the long chain fatty tertiary amine product comprise a paraffin content of from 0 wt % to about 90 wt % by weight of the long chain fatty tertiary amine product.

23. The process of claim 1 wherein the long chain fatty tertiary amine product is selected from the group consisting of trioctylamine, tridecylamine, tridodecylamine, didodecylmethylamine, ditetradecylmethylamine, dihexadecylmethylamine, dioctadecylmethylamine, decyldimethylamine, dodecyldimethylamine, tetradecyldimethylamine, hexadecyldimethylamine, octadecyldimethylamine, and mixtures thereof.

24. The process of claim 1 wherein the long chain fatty tertiary amine product comprises the following structure:

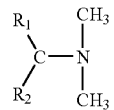

wherein $R_1$ and $R_2$ are linear or semi-linear hydrocarbons with a chainlength of 1 to 20 carbon atoms.

25. The process of claim 1 wherein step (b) comprises an initiator selected from ozone, lauroyl peroxide, or t-butyl peroxide at a concentration of 10-2000 ppm to result in a primary or secondary alkylbromide.

26. The process of claim 1 wherein step (b) is at a temperature of 5-60° C.; a pressure of 0.1-1 MPa, and reaction time of 0.1-5 hours.

27. The process of claim 26 wherein the pressure is from 0.5-1 MPa and the temperature is from 15-25° C.

28. The process of claim 25 wherein the reaction of the primary alkylbromide product is conducted at a temperature of 25-65° C. and a pressure of 0.2-5.5 MPa.

29. The process of claim 25 wherein the reaction of the secondary alkylbromide product is conducted at a temperature of 70-145° C. and a pressure of 0.2-5.5 MPa.

30. The process of claim 25 wherein the molar ratio of primary or secondary amine to primary or secondary alkylbromide product is from 1:1 to 25:1 moles.

31. The process of claim 25 wherein the reaction time is from about 0.1 to about 5 hours.

32. The process of claim 25 wherein step (b) further comprises the step of mixing water and sodium hydroxide with the primary or secondary alkylbromide product to liberate the long chain internal fatty amine product.

33. The process of claim 1 wherein optional step (c) is present and the purified long chain internal fatty amine product of step (c) comprises from about 95 wt % to about 100% by weight of the purified long chain internal tertiary amine product of a long chain fatty amine.

34. The process of claim 2 wherein step (d) comprises mixing 5-70 wt % hydrogen peroxide, 0.3-2.5 wt % of a bicarbonate material, optionally water, and the purified long chain internal fatty amine product to produce a 30-38 wt % long chain internal fatty amine oxide product.

35. The process of claim 34 wherein step (d) has a temperature of about 40-100° C. and a pressure of about 0.1 MPa.

36. The process of claim 34 wherein step (d) is continued until the hydrogen peroxide is less than 1 wt % of the original level of hydrogen peroxide added.

37. The process of claim 34 wherein step (d) is continued until the hydrogen peroxide is less than 0.1 wt % of the original level of hydrogen peroxide added.

38. The process of claim 34 wherein step (d) further comprises 0.1-5 wt %, by the combined weight of the hydrogen peroxide, the bicarbonate material, and the purified long chain internal fatty amine product, of platinum on alumina catalyst.

* * * * *

UNITED STATES PATENT AND TRADEMARK OFFICE
CERTIFICATE OF CORRECTION

PATENT NO. : 7,342,136 B2  
APPLICATION NO. : 11/272275  
DATED : March 11, 2008  
INVENTOR(S) : Corey James Kenneally et al.

It is certified that error appears in the above-identified patent and that said Letters Patent is hereby corrected as shown below:

<u>Column 3</u>

Line 50, delete "catayists" and insert -- catalysts --.

Line 53, delete "AMBERLYSTTM$^{TM}$" and insert -- AMBERLYST$^{TM}$ --.

<u>Column 5</u>

Line 56, delete "paraffiii/olefin" and insert -- paraffin/olefin --.

<u>Column 10</u>

Line 28, delete the parenthesis after "36".

Line 40, delete "zeolile" and insert -- zeolite --.

Signed and Sealed this

Eighth Day of July, 2008

JON W. DUDAS  
*Director of the United States Patent and Trademark Office*